US00PP14162P29

(12) United States Plant Patent
Verwer

(10) Patent No.: US PP14,162 P2
(45) Date of Patent: Sep. 23, 2003

(54) DAHLIA PLANT NAMED 'GALLERY BELLINI'

(75) Inventor: Aad W. M. Verwer, Lisse (NL)

(73) Assignee: Verwer Dahlias BV, Lisse (NL)

( * ) Notice: Subject to any disclaimer, the term of this patent is extended or adjusted under 35 U.S.C. 154(b) by 0 days.

(21) Appl. No.: 10/223,515

(22) Filed: Aug. 19, 2002

(51) Int. Cl.[7] ..... A01H 5/00

(52) U.S. Cl. ..... Plt./321

(58) Field of Search ..... Plt./321

(56) References Cited

PUBLICATIONS

Upov–Rom Plant Variety Database 2002/05, hit on 'Gallery Bellini' QZ PBR 010301, Apr. 15, 2001.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Dahlia plant named 'Gallery Bellini', characterized by its compact and rounded plant habit; freely branching growth habit; early and freely flowering habit; decorative inflorescence form; large inflorescences with red purple-colored ray florets; and good post-production longevity and garden performance.

1 Drawing Sheet

Botanical classification/cultivar designation: Dahlia hybrida cultivar Gallery Bellini.

BACKGROUND OF THE INVENTION

The present Invention relates to a new and distinct cultivar of Dahlia plant, botanically known as Dahlia hybrida and hereinafter referred to by the name 'Gallery Bellini'.

The new Dahlia is a product of a planned breeding program conducted by the Inventor in Lisse, The Netherlands. The objective of the breeding program is to create new potted Dahlia cultivars with compact plant habit, freely branching growth habit, early and freely flowering habit, decorative inflorescence form, attractive ray floret coloration, and good postproduction longevity and garden performance.

The new Dahlia is a naturally-occurring whole plant mutation of the Dahlia hybrida cultivar Gallery Pablo, disclosed in U.S. Plant Pat. No. 10,599. The new Dahlia was discovered and selected by the Inventor as a single flowering plant within a population of plants of the cultivar Gallery Pablo in a controlled environment in Lisse, The Netherlands, in the summer of 1999. The selection of this plant was based on its unique ray floret coloration.

Asexual reproduction of the new Dahlia by cuttings was first conducted in Lisse, The Netherlands in February, 2000. Asexual reproduction by cuttings has shown that the unique features of this new Dahlia are stable and reproduced true to type in successive generations.

SUMMARY OF THE INVENTION

The cultivar Gallery Bellini has not been observed under all possible environmental conditions. The phenotype may vary somewhat with variations in environment such as temperature and light intensity without, however, any variance in genotype.

The following traits have been repeatedly observed and are determined to be the unique characteristics of 'Gallery Bellini'. These characteristics in combination distinguish 'Gallery Bellini' as a new and distinct Dahlia cultivar:

1. Compact and rounded plant habit.
2. Freely branching growth habit.
3. Early and freely flowering habit.
4. Decorative inflorescence form.
5. Large inflorescences with red purple-colored ray florets.
6. Good postproduction longevity and garden performance.

Plants of the new Dahlia differ primarily from plants of the parent, the cultivar Gallery Pablo, primarily in ray floret color as plants of the cultivar Gallery Pablo have salmon orange-colored ray florets.

Plants of the new Dahlia can be compared to plants of the cultivar Vanessa, not patented. In side-by-side comparisons conducted in Lisse, The Netherlands, plants of the new Dahlia were more compact and were more freely flowering than plants of the cultivar Vanessa. In addition, plants of the new Dahlia and the cultivar Vanessa differed slightly in ray floret coloration.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia. The photograph comprises a side perspective view of typical flowering plants of 'Gallery Bellini'.

DETAILED BOTANICAL DESCRIPTION

In the following description, color references are made to The Royal Horticultural Society Colour Chart, 1995 Edition, except where general terms of ordinary dictionary significance are used. The aforementioned photograph and the following observations and measurements describe plants grown and flowered during the summer and early autumn of 2001 in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three weeks after planting rooted cuttings. Plants were about four months old when the photographs and the description were taken.

Botanical classification: Dahlia hybrida cultivar Gallery Bellini.

Parentage: Naturally-occurring whole plant mutation of Dahlia hybrida cultivar Gallery Pablo, disclosed in U.S. Plant Pat. No. 10,599.

Propagation:

*Type.*—By vegetative cuttings.

*Time to initiate roots.*—Summer and winter: About 5 days at 17° C.

*Time to produce a rooted young plant.*—Summer: About 14 days at 17° C. Winter: About 17 days at 17° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type potted Dahlia. Compact and rounded plant habit; upright and somewhat outwardly spreading. Freely branching habit, about six lateral branches develop after pinching; dense and full plants. Vigorous.

*Plant height.*—About 25 cm.

*Plant diameter.*—About 25 cm.

*Lateral branch description.*—Length: About 20 cm. Diameter: Towards base: About 2.7 cm. Towards apex: About 3 mm. Internode length: About 1.1 to 4 cm. Strength: Strong. Texture: Glabrous, smooth. Color: 146C.

*Foliage description.*—Arrangement: Leaves opposite; leaves may be single or compound with three or five leaflets. Shape: Elliptic. Apex: Acute. Base: Attenuate. Margin: Irregularly serrate; sinuses divergent. Length: Single leaves: About 6 cm. Compound leaves with three leaflets: About 12 cm. Compound leaves with five leaflets: About 18 cm. Width: Single leaves: About 2.8 cm. Compound leaves with three leaflets: About 5.4 cm. Compound leaves with five leaflets: About 9 cm. Venation pattern: Pinnate. Texture, upper and lower surfaces: Smooth, glabrous. Color: Young foliage, upper surface: 137B. Young foliage, lower surface: Close to 191A. Fully expanded foliage, upper surface: Close to 137A. Fully expanded foliage, lower surface: 191A. Venation, upper surface: 146D. Venation, lower surface: 145C. Petiole length: About 3.5 cm. Petiole diameter: About 2.6 mm. Petiole color, upper and lower surfaces: 146C.

Inflorescence description:

*Appearance.*—Decorative inflorescence form; inflorescences roughly hemispherical in profile. Inflorescences borne on terminals, arising from leaf axils, positioned above the foliage. Ray and disc florets develop acropetally on the receptacle. Inflorescences not fragrant. Inflorescences persistent.

*Flowering response.*—Flowering recurrent to continuous during the summer and autumn in The Netherlands. Plants start flowering about 60 days after planting.

*Postproduction longevity.*—On the plant, inflorescences maintain good color and substance for about 18 days in an outdoor environment. As cut flowers, inflorescences maintain good color and substance for about six days in an indoor environment.

*Quantity of inflorescences per flowering stem.*—About one open inflorescence and one open inflorescence bud per flowering stem; about 45 inflorescences per plant develop during the growing season.

*Inflorescence size.*—Diameter: About 11 cm. Depth (height): About 5 cm. Diameter of disc: About 3 cm. Receptacle diameter: About 4 cm. Receptacle height: About 1.5 cm.

*Inflorescence buds.*—Length: About 1 cm. Diameter: About 1.5 cm. Shape: Oblate. Color: 151A.

*Ray florets.*—Length, fully developed: About 5 cm. Width, fully developed: About 1.8 cm. Orientation: Initially upright, outer florets perpendicular to the peduncle to somewhat reflexed. Shape: Elliptic. Aspect: Longitudinal axis concave; apex weakly recurved. Apex: Emarginate, somewhat fringed. Base: Attenuate. Margin: Entire. Texture, upper and lower surfaces: Smooth, glabrous. Number of ray florets per inflorescence: About 152 arranged in about 19 rows. Venation pattern: Parallel. Color: When opening, upper surface: Towards the apex, 67A; towards the base, 1B. When opening, lower surface: Towards the apex, 67B; towards the base, 1C. Fully opened, upper surface: Towards the apex, 2C overlain with 68A to 68B; towards the margin, 2C overlain with 67A; towards the base, 1C. Fully opened, lower surface: Towards the apex, 68B; towards the base, 159D.

*Disc florets.*—Number of disc florets per inflorescence: About 20. Shape: Tubular, elongated. Apex: Five-pointed. Base: Attenuate. Length: About 6 mm. Width: At the apex, about 0.7 mm; at the base, about 0.5 mm. Color: Immature: 4C. Mature: Apex: 1C. Mid-section: 17A. Base: 4B.

*Phyllaries.*—Quantity: One whorl with about eight phyllaries. Shape: Roughly ovate. Apex: Acuminate. Base: Attenuate. Margin: Entire. Length: About 2 cm. Width: About 3 mm. Texture, upper and lower surfaces: Smooth, glabrous; leathery. Color, upper and lower surfaces: 144A.

*Peduncles.*—Length: About 20 cm. Diameter: Towards base: About 1.8 cm. Towards apex: About 1.8 mm. Angle: About 40 to 65° from vertical. Strength: Strong. Texture: Glabrous, smooth. Color: 144A.

*Reproductive organs.*—Androecium: Present on disc florets only. Stamen quantity: About five per floret. Anther shape: Linear. Anther length: About 2 mm. Anther color: 17B. Pollen amount: Scarce. Pollen color: 21B. Gynoecium: Present on ray and disc florets. Pistil quantity: One per floret. Pistil length: About 2.5 mm. Stigma shape: Lanceolate. Stigma color: Close to 13B. Style length: About 1.8 mm. Style color: 150C. Ovary color: 9C.

*Seeds/fruits.*—Seed and fruit development has not been observed.

Disease/pest resistance: Resistance to pathogens and pests common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Gallery Bellini', as illustrated and described.

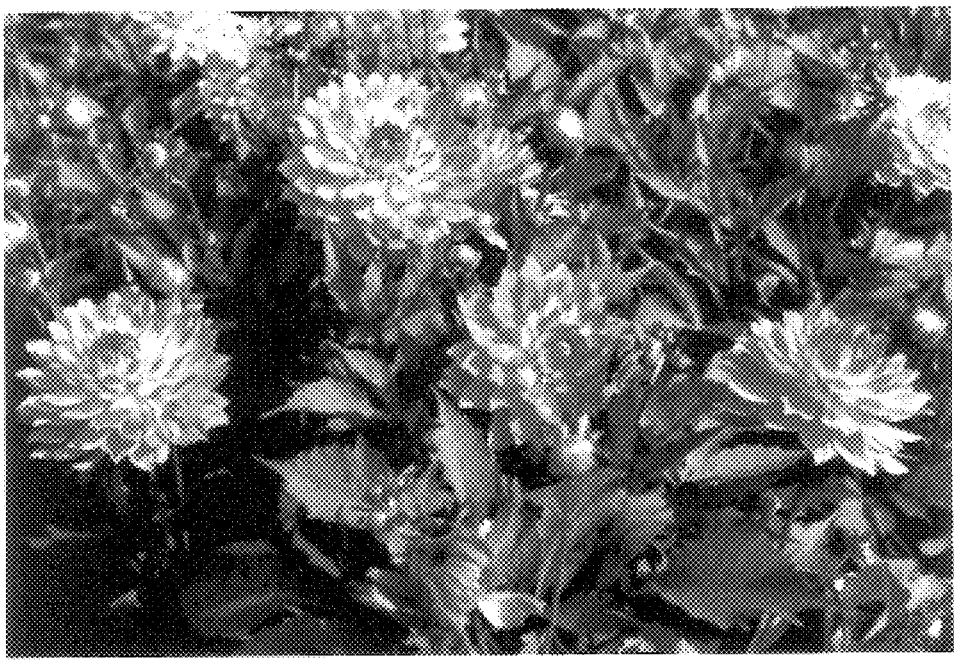

* * * * *